United States Patent
Hanly et al.

(10) Patent No.: US 6,726,672 B1
(45) Date of Patent: Apr. 27, 2004

(54) INTRAVENOUS DRUG ACCESS SYSTEM

(75) Inventors: Kevin B. Hanly, Mission Viejo, CA (US); Frank O'Brien, Rancho Palos Verdes, CA (US); Salvadore F. Palomares, Rancho Santa Margarita, CA (US); William S. Phillips, Mission Viejo, CA (US); Bruce Hubrecht, Canyon Lake, CA (US); William M. Porter, Carlsbad, CA (US); Evelyn L. Foss, Lake Forest, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 09/487,105

(22) Filed: Jan. 19, 2000

Related U.S. Application Data

(63) Continuation of application No. 09/161,942, filed on Sep. 28, 1998, now abandoned.

(51) Int. Cl.[7] .......................... A61B 19/00; A61M 5/32; A61M 37/00; B65D 39/00
(52) U.S. Cl. ...................... 604/414; 604/408; 604/415; 604/905; 604/86; 604/6.15; 215/247
(58) Field of Search .......................... 604/240, 246–7, 604/283, 403, 408, 411–12, 414, 415, 905, 86–88; 251/149.1, 149.3, 149.6; 141/329, 383

(56) References Cited

U.S. PATENT DOCUMENTS

| | | | | |
|---|---|---|---|---|
| 3,416,528 A | * | 12/1968 | Kahn | 141/329 |
| 4,346,703 A | * | 8/1982 | Dennehey et al. | 604/244 |
| 4,368,729 A | | 1/1983 | Dossin | |
| 4,607,671 A | | 8/1986 | Aalto et al. | |
| 4,673,400 A | * | 6/1987 | Martin | 604/536 |
| 4,675,020 A | | 6/1987 | McPhee | |
| 5,108,702 A | | 4/1992 | Hubner | |
| 5,188,620 A | | 2/1993 | Jepson et al. | |
| 5,190,534 A | | 3/1993 | Kendell | |
| 5,199,948 A | | 4/1993 | McPhee | |
| 5,501,676 A | * | 3/1996 | Niedospial et al. | 604/403 |
| 5,509,912 A | | 4/1996 | Vaillancourt et al. | |
| 5,533,983 A | | 7/1996 | Haining | |
| 5,549,583 A | * | 8/1996 | Sanford et al. | 604/535 |
| 5,669,891 A | | 9/1997 | Vaillancourt | |
| 5,694,686 A | | 12/1997 | Lopez | |
| 5,788,215 A | | 8/1998 | Ryan | |
| 5,817,083 A | | 10/1998 | Shemesh et al. | |
| 6,068,617 A | * | 5/2000 | Richmond | 604/255 |
| 6,261,282 B1 | * | 7/2001 | Jepson et al. | 604/533 |
| 6,394,983 B1 | * | 5/2002 | Mayoral et al. | 604/192 |
| 6,440,107 B1 | * | 8/2002 | Trombley et al. | 604/256 |
| 6,478,788 B1 | * | 11/2002 | Aneas | 604/411 |

* cited by examiner

*Primary Examiner*—Patricia Bianco
(74) *Attorney, Agent, or Firm*—Knobbe Martens Olson & Bear LLP

(57) ABSTRACT

An intravenous drug access system. In one embodiment of the invention, the drug access system includes an IV bag having an inlet port and an outlet port, whereby the inlet port is a female luer integral therewith. The integral female luer fitting may be fitted with a sealed end cap including a male luer insert with a closed end. An alternative embodiment of the present invention comprises a discrete pre-molded connector made with a spike at one end and a female luer fitting at the opposing end. The spike is used to penetrate a standard IV bag through a conventional inlet port.

12 Claims, 6 Drawing Sheets

INTRAVENOUS DRUG ACCESS SYSTEM

This application is a continuation of U.S. application Ser. No. 09/161,942, filed Sep. 28, 1998, now abandoned, which is incorporated herein by reference.

FIELD OF THE INVENTION

The invention relates to the field of fluid transfer devices and, more specifically, to a novel intravenous drug access system.

BACKGROUND OF THE INVENTION

The manipulation of fluids for administration to a patient in hospital and medical settings involves the use of drug access systems that typically include a sealed inflatable container, commonly referred to as an intravenous (IV) bag. The IV bag is used to store a primary liquid such as plasma, blood, saline, or other types of medicinal solutions. When fluids are to be introduced into a patient intravenously, an IV bag is suspended above the patient on a portable hanger stand. Through a series of tubes and connectors, the fluid within the IV bag is delivered from the IV bag to the patient.

FIG. 1 illustrates a partial perspective view of a traditional IV bag 100. The IV bag includes a sealed inlet or injection port 102 and an outlet port 104 for the transfer of fluids to and from the IV bag, respectively. The inlet port 102 permits the introduction of a secondary fluid, such as a drug, into the IV bag, for mixing with the primary fluid. The outlet port 104 permits the transfer of the primary solution in the IV bag to the patient via tubes and connectors.

To seal the contents of the bag, the inlet port 102 typically includes a septum 106 compressively affixed within the interior opening of the inlet port to prevent the flow of fluid out of the bag. The septum 106 may be of continuous construction or made with a pre-fabricated slit that remains closed until penetrated. In either case, the septum is sufficiently resilient so as to permit penetration of the septum with a sharp device such as a syringe needle for the transfer of fluids into the IV bag.

Another example of a sharp device for penetrating a septum within an inlet port is a spiked connector. One type of spiked connector is a dual-spiked connector comprising a housing having a conduit extending from one spike to the other. The first spike is open-ended, in which the conduit communicates with the ambient. The second spike, at the opposite end of the connector, is closed such that the conduit is not in communication with the ambient. This closed-end tip is designed to break away and is used to penetrate the IV bag through the inlet port. At the first end, the open-ended spike is used to penetrate a drug vial containing a secondary fluid. By placing this dual-spiked connector between a drug vial and the W bag, a secondary fluid can be introduced into the IV bag and mixed with the primary fluid therein.

As a discrete pre-fabricated component, such a dual-spiked connector does not permit fluid flow therethrough because at least one spike includes a closed, break-away tip. However, upon penetration of the closed spike tip through the inlet port of the IV bag, fluid communication between the secondary fluid container and the bag may be established by breaking off the break-away tip while the tip is within the interior of the IV bag. Once the tip is broken, the conduit of the connector permits the flow of fluid in the internal fluid conduit from the drug vial to the interior of the IV bag. Disadvantageously, the break-away tip floats in the IV bag during the administration of the primary and secondary fluids to the patient through the outlet port. Should the break-away tip become lodged in the outlet port of the IV bag, the flow of the primary and secondary fluids to the patient may be stopped or dramatically reduced, endangering the health of a patient. Moreover, because the mixed solution in the IV bag is visible to the patient, the existence of the floating foreign object (spike tip) in the fluid may be psychologically troubling to the patient.

Another type of dual-spiked connector for introducing a secondary fluid into an IV bag is one that eliminates the break-away tip. With this alternative connector, the conduit is in communication with the ambient at both spiked ends. Instead of a breakaway tip, however, this alternative connector employs a plug centrally positioned within the internal conduit to prevent the flow of fluid therethrough until the medical practitioner so desires. After both spikes of the connector are in place, i.e., both have penetrated their respective medical containers, the medical practitioner applies an external compressive force to the plug by squeezing the IV bag. The force applied dislodges the plug, whereby the plug is forced into the secondary fluid container (drug vial).

The use of a push-away plug also presents problems. For example, it has been proven difficult, if not costly, to manufacture a conduit plug that reliably performs as designed. If the conduit plug is made too small, the plug does not exert sufficient frictional force against the interior walls of the internal conduit. Under those circumstances, the ambient pressure from the primary fluid itself may dislodge the primary plug prematurely, causing leakage of fluid intended for a patient. Alternatively, if the conduit plug is too large, the compressive force that is necessary to dislodge the plug is too great. Under those circumstances, the force applied externally to the IV bag may adversely compromise the structural integrity of the bag, again causing life-sustaining fluid to leak.

With either of the above connectors, an inherent problem exists in that once fluid flow is established, it cannot be stopped. That is because neither connector is adapted to control the fluid flow therethrough. Moreover, the configuration of the connectors is such that a fluid-control valve cannot be readily attached to the exposed spike end of the connector. Valves that exist to control the flow of medicinal fluids into an IV bag, such as that shown in U.S. Pat. No. 5,694,686, have male luer fittings that are not designed to connect to a spike (e.g. the CLAVE® 1000 connector manufactured by ICU Medical, Inc. of San Clemente, Calif. or the pre-slit Injection Site manufactured by McGaw Inc. of Irvine, Calif.) Thus, a device to permit an IV bag to be placed in fluid communication with a wide range of commercially available connectors is needed.

Another problem with the connectors identified above is that manufacturing costs are high. Typically, the connectors are injection molded. To generate the interior conduit of the connector housing, a core pin is used to define the surface of the interior conduit. Due to the extremely high temperatures used in the molding process, there is a tendency of the core pin to float within the liquified housing material during the molding process, creating non-uniform wall thickness, which is unacceptable. Thus, the rejection rate is high, driving up the costs of manufacture.

There is, therefore, a need for a drug access system configured to eliminate break-away or floating parts, to reduce the cost of part manufacture, and to expand the use of connectors to which an IV bag may be attached.

SUMMARY OF THE INVENTION

The drug access system of the present invention has several features, no single one of which is solely responsible for its desirable attributes. Without limiting the scope of this invention, as expressed by the claims which follow, its more prominent features will now be discussed briefly.

The present invention is an intravenous drug access system. In one embodiment of the invention, the drug access system includes an IV bag having an inlet (injection) port and an outlet port, whereby the inlet port is a female luer fitting integral with the IV bag. With a female luer fitting integral with the IV bag, any number of one-way valves or needleless syringes may be connected to the female luer fitting to facilitate and control the flow of fluid into or out of the IV bag. With a one-way valve connected to the female luer, the IV bag of the present drug access system may be filled with primary fluid and shipped to the end user for later introduction of a secondary fluid. In this embodiment, breakaway parts and/or push-away plugs are advantageously eliminated.

Where it is desired that the IV bag be filled and shipped without a one-way valve already attached thereto, the integral female luer fitting may be enclosed with a sealed end cap comprising a male luer insert with a closed end. Upon receipt by the end user, the IV bag may be turned upside down to isolate the inlet port away from the contents of the IV bag so that the end cap may be removed and replaced by any valve or connector chosen by the end user. In a variation of this embodiment, the female luer fitting may include a thin, membrane stretched across the opening of the female luer fitting to prevent the flow of fluid therethrough. It is contemplated that the membrane be readily penetrable by the application of a male luer fitting of a valve by the end user when desired. With this latter variation, no end cap is required and the IV bag need not be turned upside down to connect the valve thereto.

The advantage of an integral female luer with an IV bag is that it eliminates the need for a costly conventional dual-spiked connector. However, if a user would prefer to receive IV bags that have conventional inlet ports, an alternative embodiment of the present invention comprises a discrete pre-fabricated connector made with one spike at one end and a female luer fitting at the opposing end. The spike is used to penetrate the IV bag through the conventional inlet port, as with the prior art connectors. Instead of having a second spike, however, an integral female luer is provided that permits connection to a one-way valve or needleless syringe, or any other connector having a male luer fitting. In one variation of this second embodiment, the improved connector includes a protective flange that surrounds, at least in part, the spike to prevent the spike from inadvertently coming into contact with other objects and becoming contaminated when the connector is not in use. In addition, the flange prevents the spike from piercing the skin of a healthcare worker.

There are additional advantages to this second embodiment. In the molding process of the prior art connectors, there were high rejection rates, as explained above. With a connector having a female luer fitting at one end, instead of a second spike, the core pin may be more effectively secured, reducing the likelihood of the core pin floating during the molding process. This results in a reduction in the cost of manufacture, when compared to the molding of prior art connectors. Unlike the prior art connectors, the spike contemplated in the second embodiment of the present invention need not be a closed tip spike. In other words, the spike can be open-ended, permitting immediate backflow of the primary fluid in the IV bag into the interior conduit of the inventive connector. In that instance, the female luer fitting at the other end may be provided with an end cap or thin membrane, as described above, to prevent the fluid from leaking. Upon the connection of a one-way valve or a needleless syringe, fluid flow may be established between a secondary fluid source and the IV bag.

DETAILED DESCRIPTION OF THE PREFERRED EMBODIMENTS

The following detailed description is directed to certain specific embodiments of the invention. However, the invention can be embodied in a multitude of different ways as defined and covered by the claims. In this description, reference is made to the drawings wherein like parts are designated with like numerals throughout.

Figure 1:
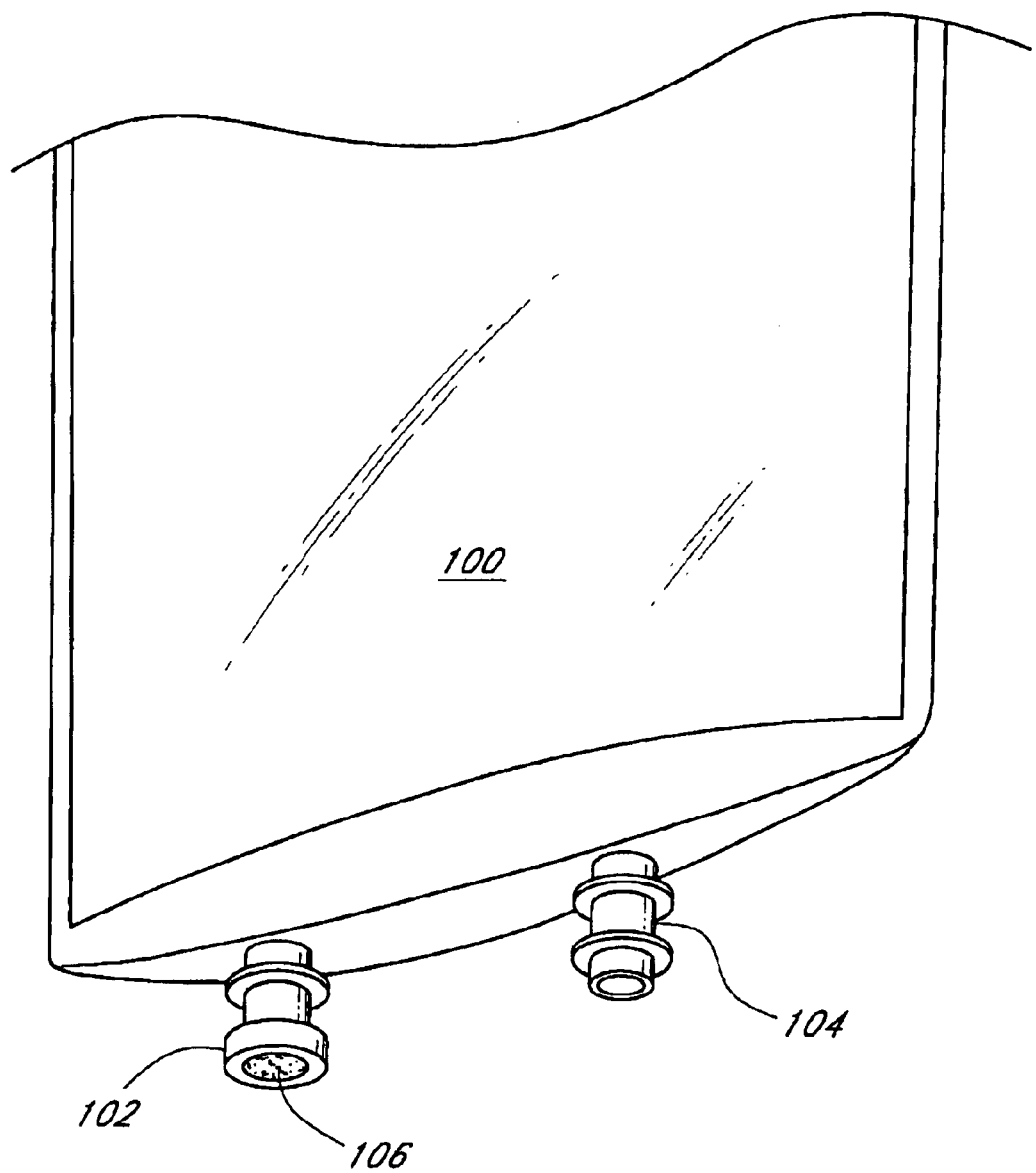
FIG. 1 is a perspective view of a conventional intravenous bag that houses fluids for introduction into patients.
Figure 2:
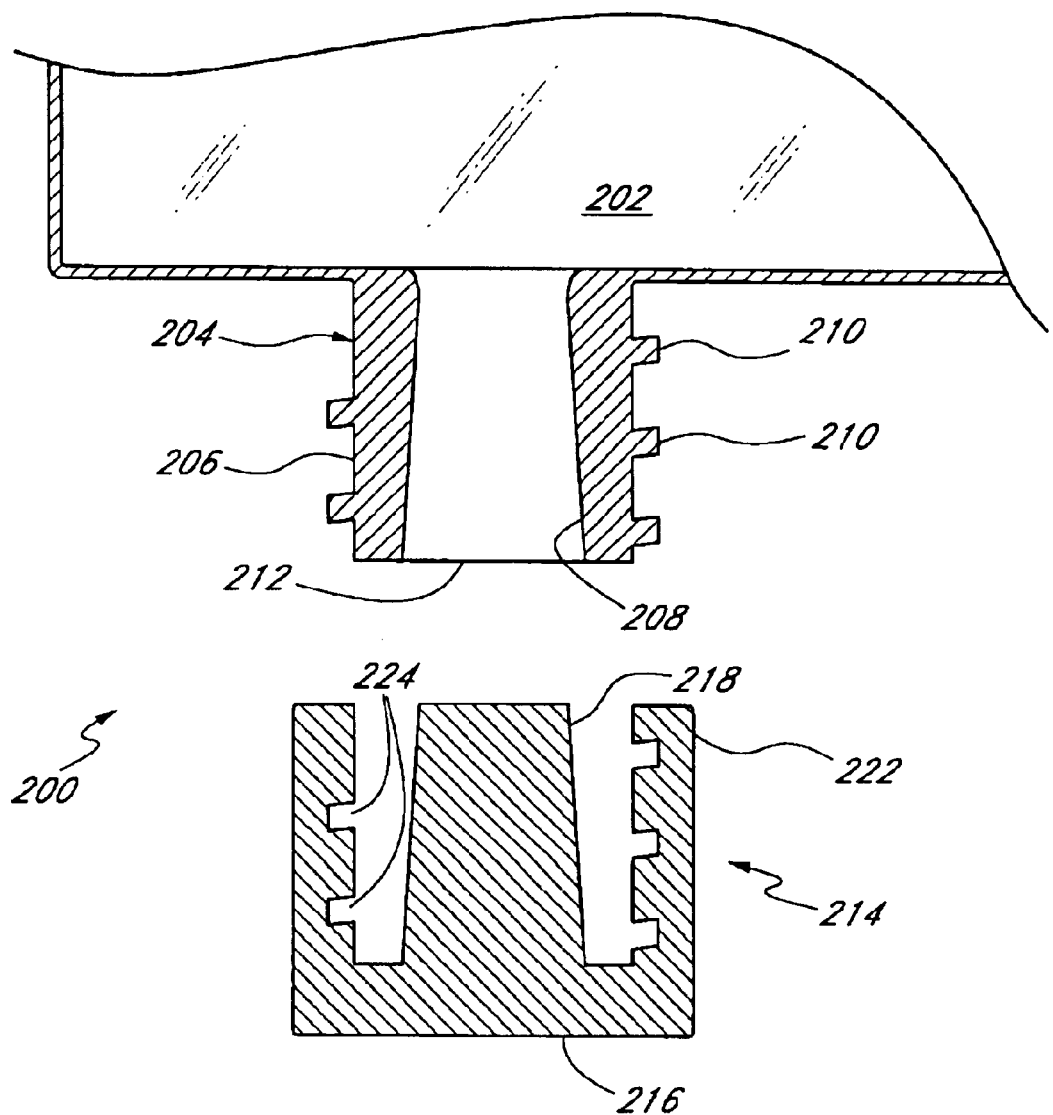
FIG. 2 is an elevational sectional view of a first embodiment of the present invention.

As discussed above, FIG. 1 shows a conventional IV bag having inlet and outlet ports for the transmission of fluids into the IV bag and to the patient, respectively. FIG. 2 illustrates a first embodiment of the drug access system 200 of the present invention, which is an improvement over the prior art IV bag. The inventive drug access system 200 comprises a collapsible container 202, such as an IV bag, that includes at least one integral inlet (injection) port 204 and at least one integral outlet port (not shown). The inlet port 204 comprises a housing 206 made of, e.g., a hard durable plastic, metal, or any other material known to those of skill in the art. The port 204 defines an internal conduit 208 for allowing fluid communication between the IV bag 202 and a discrete connector or valve. The housing 206 has a female fitting at a distal end, commonly referred to as a female luer, for acceptance of a male luer therein. Preferably, the housing 206 includes external threads 210 for mating with a male luer lock. The female luer inlet port 204 may be made integral with the IV bag 202 by methods known in the art of manufacturing IV bags.

To seal the contents of the IV bag 202, a male luer cap 214 may be used. The male luer cap 214 consists of a housing 216 defining a solid plug 218 that fits within the interior conduit 208 of the female luer inlet port 204. Preferably, the male luer cap 214 includes an annular collar 222 having internal threads 224 for mating with the threads 210 of the housing 206. If desired, the interior conduit 208 and the corresponding mating plug 218 may be tapered to permit a more snug fit. Upon receipt by the end user, the IV bag 202 may be turned upside down, as will be understood by those skilled in the art, in order to isolate the inlet port 204 away from the contents of the IV bag 202. At that point, the user may remove the end cap 214 and replace it with a valve or connector having a male luer.

In one variation of this embodiment, the housing 206 may come fitted with a thin membrane made of, e.g., latex (not shown) across an opening 212 of the internal conduit 208 to prevent the flow of fluid therethrough. It is contemplated that the thin membrane be readily penetrable by the application of a mating male luer of a valve or needleless syringe by the end user when desired. In a second variation, a compressible seal (not shown) may be provided within the opening 212 of the housing 206, wherein the seal has a pre-fabricated slit therein that remains closed until the seal is compressed by the application of a male luer into the opening 212. With these latter variations, no cap is necessary and the IV bag 202 need not be turned upside down to connect the valve thereto. The membrane and seal may be manufactured by known methods used by those of skill in the industry.

Figure 3:
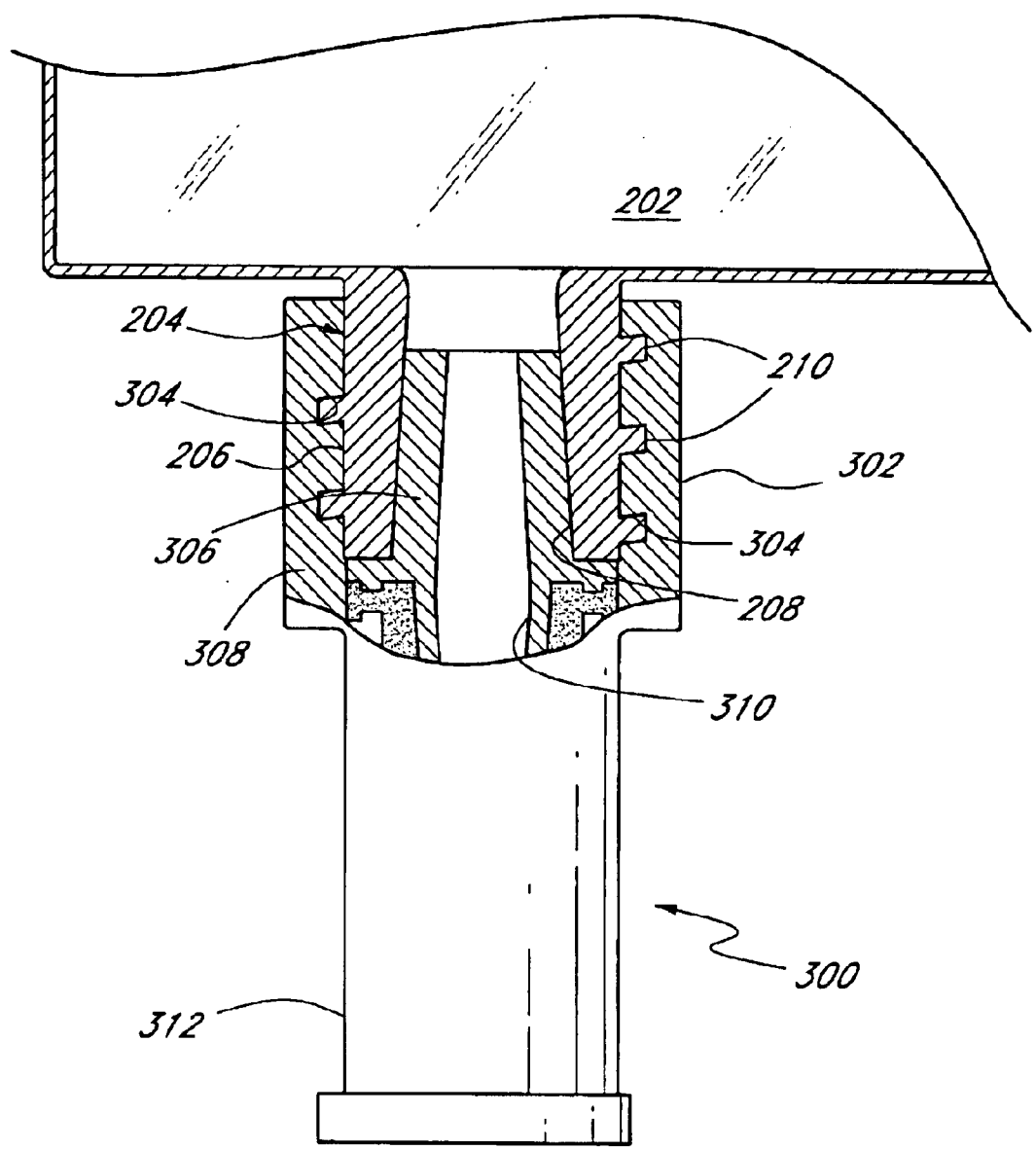
FIG. 3 is an elevational sectional view of the first embodiment of FIG. 2 shown with a needleless valve in fluid communication therewith shown in partial cross-section.

Once the male luer cap 214 is removed, the female luer inlet port 204 of the IV bag 202 may be advantageously mated with various male luer connectors or valves. For example, referring to FIG. 3, the IV bag 202 may be mated to a needleless valve 300, such as the CLAVE® 1000 connector manufactured by ICU Medical, Inc. of San Clemente, Calif. A first, proximal end 302 of the needleless valve 300 includes a male luer fitting 306 for mating with the female luer inlet port 204 of the IV bag 202. The needleless valve 300 may be provided with an annular collar 308 having internal threads 304 to mate with the external threads 210 of the female luer inlet port 204. An internal conduit 310 extends through the valve. A second, distal end 312 of the needleless valve 300 preferably includes a seal (not shown) that encloses an opening at the distal end from the internal conduit to the ambient. The seal prevents the flow of liquid through the valve until a male luer connector (not shown) is mated to the second, distal end 312 of the needleless valve 300. The connection of a male luer connector to the distal end 312 of the valve exposes the opening to permit fluid therethrough, as described in greater detail in U.S. Pat. No. 5,694,686 to Lopez, incorporated herein by reference. Once the needleless valve 300 is connected to the female luer inlet port 204, a sealed fluid pathway is created, as will be understood by those of skill in the art.

It is contemplated that any number of valves or connectors may be connected to the female luer inlet port 204 of the IV bag 202 of intravenous drug access system 200. For example, the female luer inlet port 204 may be mated with a pre-slit Injection Site connector having a male luer fitting. The pre-slit Injection Site connector may include a septum, such as an elastomeric plug, to act as a seal. The septum can be penetrated by a sharp piercing member such as a cannula, a syringe, or other medical implement. As with a needleless valve, the use of a pre-slit Injection Site connector advantageously permits a user to control the flow of liquid to or from the IV bag 202.

Figure 4:
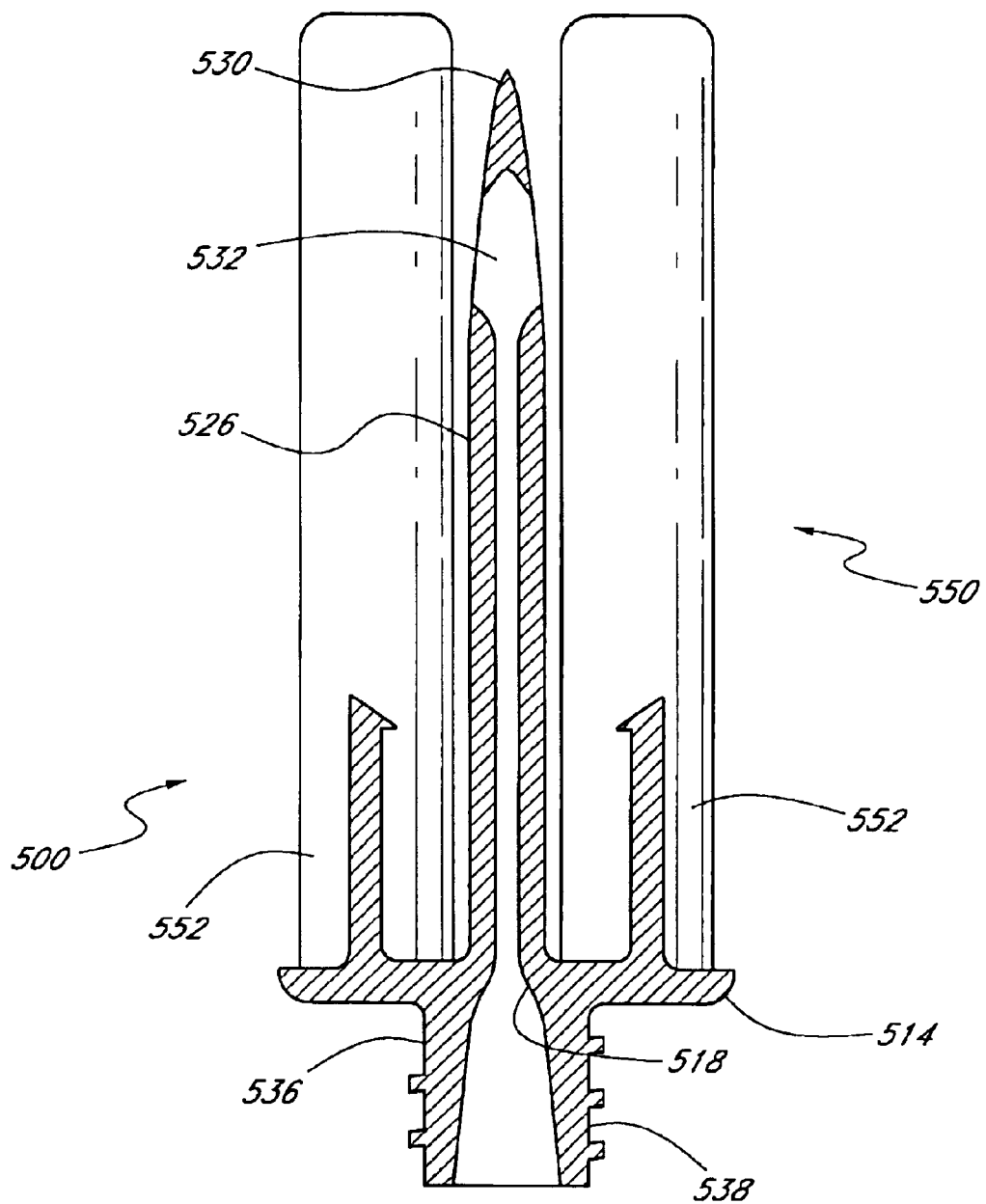
FIG. 4 is an elevational sectional view of the second embodiment of the present invention.
Figure 5:
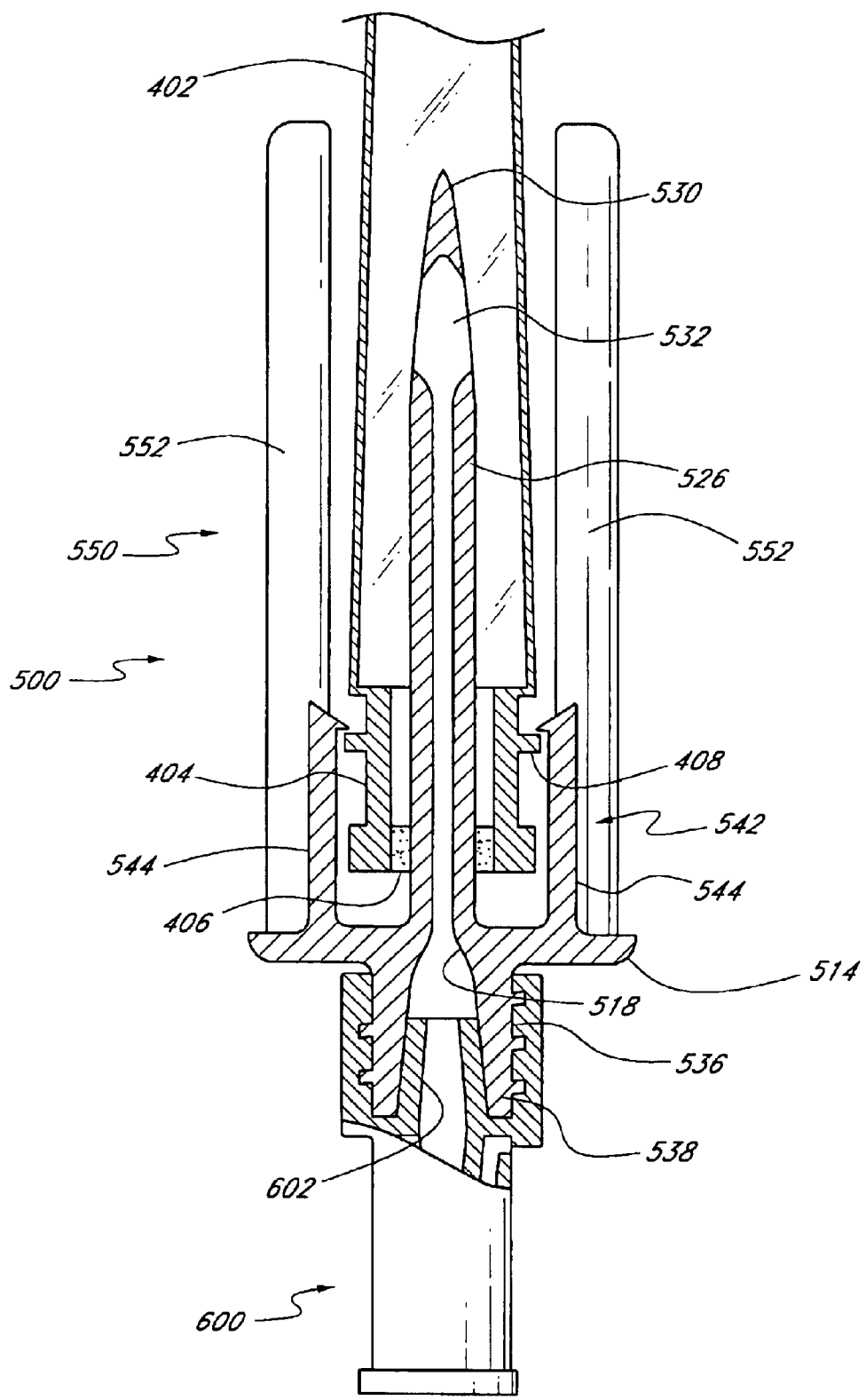
FIG. 5 is an elevational sectional view of the second embodiment of FIG. 4 shown applied to an IV bag and a valve shown in partial cross-section.

With reference to FIGS. 4 and 5, a second embodiment of the invention comprises a connector 500 for providing fluid communication between a medical connector or valve 600 and an IV bag 402 having a conventional sealed inlet (injection) port 404. The inlet port 404 of the IV bag 402 includes a conventional septum 406 within the interior of the inlet port 404 to prevent the flow of fluid out of the IV bag 402. An annular locking member 408 extends radially from a midsection of the inlet port 404. The annular locking member 408 may be used to lock a valve or connector to the inlet port 404, as described in further detail below.

Preferably, the medical connector 500 includes a main housing 514 that is preferably integrally molded from a suitable plastic material, such as polycarbonate, although other medically inert materials may be used. The housing 514 defines an internal fluid conduit 518 having a first, proximal end with a spike or puncture member 526. The spike 526 is configured for piercing or spreading apart the sealed inlet port 404 of the IV bag 402. The spike 526 preferably includes a sharp tip 530 having at least one aperture 532 near or at the tip 530 of the spike 526. The aperture 532 permits fluid from the conduit 518 to the IV bag 402. The aperture 532 is preferably open to the ambient, although a removable closure feature, such as a break-away tip or a push-away plug, is also contemplated.

A second, distal end 536 of the connector 500 preferably defines a female fitting, such as a female luer 538. The female luer 538 is contemplated to be configured as described above in association with the first embodiment of the present invention. As with the female luer fitting of the first embodiment (FIG. 3), the female luer fitting of the present invention connector 500 may also be mated with a valve 600 having a male luer 602 (FIG. 5). The desired connection is as described above in association with FIG. 3. Alternatively, a pre-slit Injection Site connector or a needleless syringe may be mated with the connector 500 in lieu of a needleless valve. Any valve or connector that has a male luer may be used in connection with the medical connector 500.

Preferably, the housing 514 also includes an interlocking coupling 542 for use in locking the connector 500 to the standard inlet (injection) port 404. It is contemplated that the interlocking coupling 542 comprises resilient fingers 544 that snap over the annular locking member 408 of the inlet port 404. At the end of each finger 544 is a lip that extends inward to provide a seat for the annular locking member 408 of the inlet port 404. Preferably, there are at least three fingers 544 of the interlocking coupling 542. As the medical connector 500 is directed toward the IV bag 402, the annular locking member 408 bears against the ends of the fingers 544, pushing them outward. After the annular locking member 408 has passed the lips of each finger, the fingers return to their normal position for a snap fit. At that point, the spike 526 has penetrated the septum 406 of the inlet port 404 to establish fluid connection therewith.

It is also desirable that an annular protective collar 550 surround the spike 526 to prevent contact of the spike with a contaminated surface prior to use. The protective collar 550 further reduces the risk that medical personnel are injured by exposure to the spike 526. The protective collar may comprise discrete flanges 552 arranged radially about the spike 526. Preferably, the protective flanges 552 extend axially past the termination point of the spike 526, thereby allowing the connector 500 to be placed on a resting surface, if desired. When applied to an IV bag, the protective collar 550 straddles the base of the IV bag 402, as shown in FIG. 5. Thus, the IV bag 402 is positioned between adjacent flanges 552 of the collar 550. Of course, it will be understood by one of skill in the art that it is not necessary to have an annular protective collar at all, if so desired.

In a variation of this embodiment, the fingers 544 of the interlocking coupling 542 may be made integral with the protective flanges 552 instead. In that variation, each flange has at least one finger extending inwardly therefrom for locking engagement with the annular locking member 408 of the inlet port 404.

If the medical connector 500 is to be connected to the IV bag 402, which has been shipped pre-filled with a fluid, it is recommended that a needleless valve 600, such as the CLAVE® 1000 connector, be affixed to the second end 536 of the medical connector 500. Other valves or closures having a male luer fitting may also be used, as will be understood by those of skill in the art.

Figure 6A:
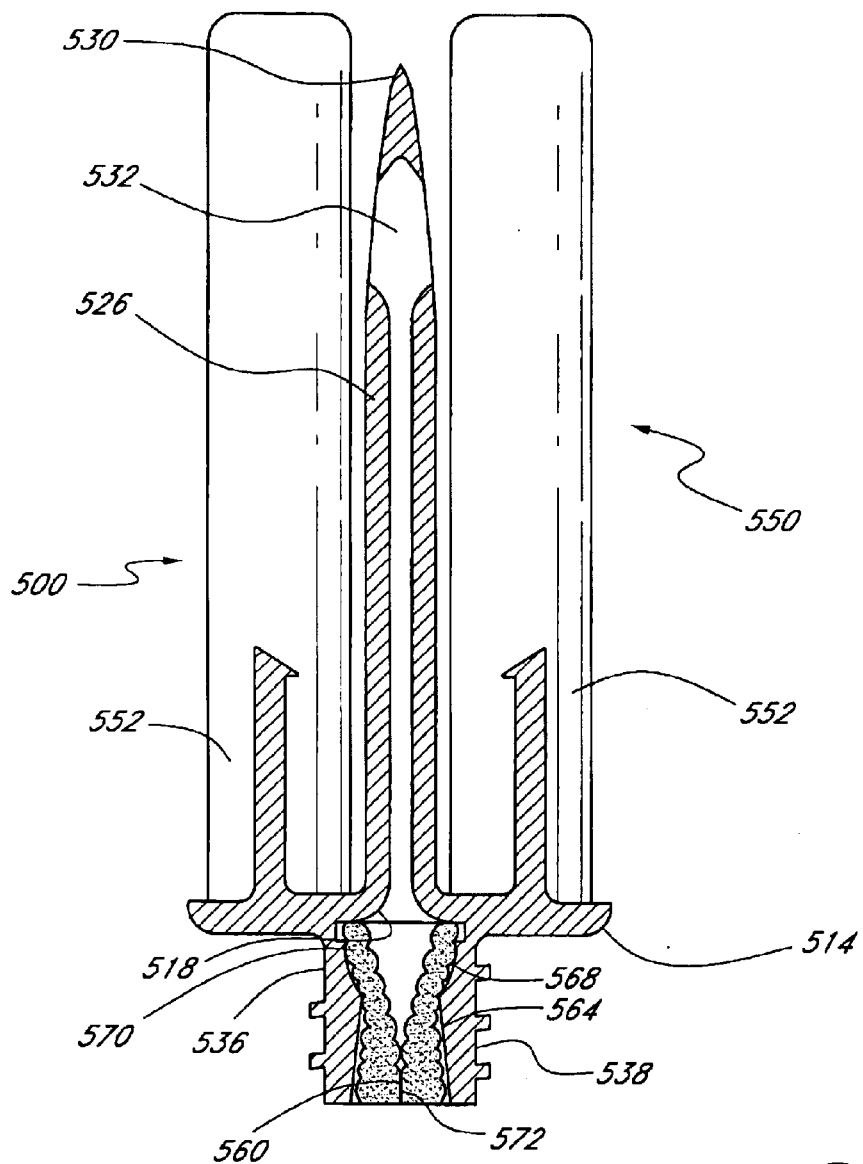
FIG. 6A is an elevational sectional view of a variation of the second embodiment of FIG. 4, illustrating an integral seal.
Figure 6B:
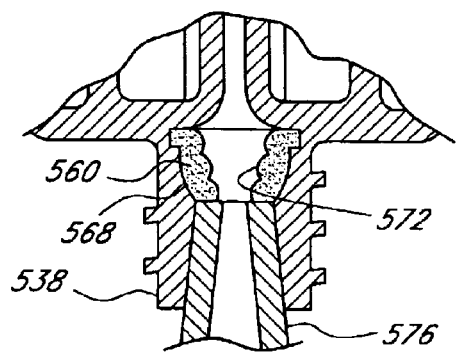
FIG. 6B is an elevational sectional view of the embodiment of FIG. 6A, illustrating the integral seal compressed by a male luer connector.

A further variation of the embodiment of FIGS. 4 and 5 is shown in FIGS. 6A and 6B. In FIG. 6A, the connector 500 is all respects the same, except that the interior conduit 518 at the distal end 536 is configured to accept a conventional septum (not shown) or an integral, penetrable seal 560. In this embodiment, the interior conduit 518 at the distal end 536 is tapered to form a smaller diameter section 564 and a larger diameter section 568 spaced inwardly therefrom. The seal 560 is affixed to interior conduit 518 at the larger diameter section 568, preferably within an annular groove 570, and extends outwardly toward the outlet of the distal end 536. The seal 560 includes a pre-fabricated slit 572 that remains closed at its distal end when it is compressed within the smaller diameter section 564 of the interior conduit 518. Upon application of a male luer connector 576 (FIG. 6B) into the female luer 538 of the connector 500, the seal 560 is pushed inwardly so that the slit 572 is permitted to expand to an open position within the larger diameter section 568. When the slit 570 opens, upon application of the male luer 576 within the female luer 538, fluid communication is permitted therethrough.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The scope of the invention is indicated by the appended claims rather than by the foregoing description. All changes which come within the meaning and range of equivalency of the claims are to be embraced within their scope.

What is claimed is:

1. A medical connector for use in transferring fluids to a drug access bag having at least one inlet port, the medical connector comprising:

a housing having a first and second end each terminating an internal conduit defined therein;

a puncture member at the first end of the housing adapted to be inserted into the inlet port to permit fluid transfer between said bag and said connector;

a female luer fitting at the second end of the housing for mating with a corresponding male luer fitting of a discrete connector or valve; and a protective flange surrounding at least a portion of the puncture member to minimize contamination of said puncture member due to inadvertent contact with contaminated surfaces, wherein the protective flange comprises two discrete portions configured to straddle the drug access bag.

2. The medical connector of claim 1, wherein the female luer includes external threads surrounding said luer to form a luer lock, and the connector further comprises an interlocking coupling disposed between the protective flange and the puncture member adapted to attach the connector to an inlet port on a drug access bag.

3. The medical connector of claim 2, wherein the valve is a needleless valve.

4. The medical connector of claim 3, wherein the female luer includes a protective membrane to seal the contents of the bag therein, said membrane being penetrable by the application of a male luer into said female luer.

5. The medical connector of claim 4 further comprising a male luer end cap adapted to sealably enclose the female fitting.

6. The medical connector of claim 5 further comprising a coupling integral with the housing to receive and retain at least a portion of the inlet port.

7. The medical connector of claim 3, wherein the needleless valve comprises a cavity with a resilient seal disposed therein, the seal being adapted to be moved to a compressed position to permit fluid flow through the valve upon insertion of a medical implement, and the seal being adapted to resiliently return to an uncompressed position and obstruct fluid flow upon removal of the medical implement.

8. The medical connector of claim 1 in combination with a drug access system comprising a bag adapted to contain medicinal fluids having an inlet port and an outlet port, said outlet port configured to transfer said fluids to a patient, said inlet port constructed integral with said bag and adapted to receive fluids therethrough for introduction into said bag, said inlet port being further configured to sealably connect to the medical connector, said inlet port comprising a housing defining an internal conduct for fluid communication between said medical connector and said bag.

9. The combination of claim 8 wherein the inlet port further comprises external threads surrounding said female luer end to form a luer lock.

10. The combination of claim 9 wherein the female luer includes a protective membrane to seal the contents of the bag therein, said membrane being penetrable by the application of a male luer into said female luer.

11. The combination of claim 10 further comprising a male luer end cap adapted to sealably enclose the female luer.

12. The medical connector of claim 1, wherein said puncture member comprises a spike having a tip and at least one aperture at or near said tip.

* * * * *

UNITED STATES PATENT AND TRADEMARK OFFICE
CERTIFICATE OF CORRECTION

PATENT NO.        : 6,726,672 B1                                    Page 1 of 1
APPLICATION NO.   : 09/487105
DATED             : April 27, 2004
INVENTOR(S)       : Kevin B. Hanly et al.

It is certified that error appears in the above-identified patent and that said Letters Patent is hereby corrected as shown below:

At column 1, line 29, (Approx.), please delete "bag," and insert -- bag --, therefor.

At column 1, line 53, please delete "W" and insert -- IV --, therefor.

At column 3, line 27, (Approx.) please delete "thin," and insert -- thin --, therefor.

Signed and Sealed this

Twenty-seventh Day of November, 2007

JON W. DUDAS
*Director of the United States Patent and Trademark Office*